United States Patent [19]

Lynch

[11] Patent Number: 4,610,872
[45] Date of Patent: Sep. 9, 1986

[54] DENTIFRICE FORMULATION AND METHOD OF TREATING TEETH, MOUTH AND THROAT THEREWITH TO REDUCE PLAQUE ACCUMULATION AND IRRITATION

[75] Inventor: Matthew J. Lynch, Wilmington, Del.

[73] Assignee: ICI Americas Inc., Wilmington, Del.

[21] Appl. No.: 814,000

[22] Filed: Dec. 27, 1985

Related U.S. Application Data

[62] Division of Ser. No. 685,167, Dec. 21, 1984, Pat. No. 4,585,649.

[51] Int. Cl.$^4$ .............................................. A61K 7/16
[52] U.S. Cl. ................................................... 424/49
[58] Field of Search ................................. 424/49-58

[56] References Cited

U.S. PATENT DOCUMENTS

| | | | |
|---|---|---|---|
| 3,120,469 | 2/1964 | Tamas | 167/93 |
| 3,342,680 | 9/1967 | Treon | 167/65 |
| 3,651,208 | 3/1972 | Lauster | 424/54 |
| 3,928,555 | 12/1975 | Gault | 424/22 |
| 4,002,732 | 1/1977 | Gault | 424/49 |
| 4,082,881 | 4/1978 | Ling et al. | 424/241 |
| 4,169,152 | 9/1979 | LeMaitre et al. | 424/285 |
| 4,425,322 | 1/1984 | Harvey et al. | 424/52 |
| 4,444,747 | 4/1984 | Hayes et al. | 424/52 |
| 4,482,536 | 11/1984 | Hayes et al. | 424/52 |
| 4,525,343 | 6/1985 | Raaf | 424/54 |
| 4,585,649 | 4/1986 | Lynch | 424/49 |

Primary Examiner—Shep K. Rose
Attorney, Agent, or Firm—Richard A. Rowe

[57] ABSTRACT

Dentifrice formulations containing monoalkyl and dialkyl ethers of dianhydrohexitols in the form of toothpaste, mouthwash, chewing gums, confections, toothpicks and dental floss are effective in the treatment of oral surfaces and cavities to reduce irritation and plaque accumulation caused by the action of bacteria.

9 Claims, No Drawings

DENTIFRICE FORMULATION AND METHOD OF TREATING TEETH, MOUTH AND THROAT THEREWITH TO REDUCE PLAQUE ACCUMULATION AND IRRITATION

This is a divisional of co-pending application Ser. No. 06/685,167 filed on Dec. 21, 1984, now U.S. Pat. No. 4,585,649.

The present invention relates to the treatment of the mouth and throat to reduce irritation and plaque accumulation caused by the action of bacteria. It is particularly related to dentifrice formulations, in the form of toothpaste, gels, mouthwash, chewing gums, and confections having therapeutic and prophylactic action.

It is widely recognized that regular use of antimicrobial dentifrice combinations may significantly reduce the buildup of plaque on teeth. Plaque is the attachment of microorganisms to the pellicle which coats teeth and tongue cavities and forms a surface upon which further accumulation may grow to form hard calculus deposits. If not removed, these deposits cause inflammation of the supportive tissues of the teeth. The ensuing carious lesions account for most of the periodontal disease which may result in loosening and eventual loss of teeth.

While the mechanism for the formation of plaque remains speculative, it is generally recognized that foods containing natural sugars such as sucrose and glucose are consumed by plaque forming organisms such as *Streptococcus mutans*. Dental decay is thought to be initiated by decalcification of dental enamel by the organic acids which are produced by fermentative catabolism of sugars by bacteria such as *S. mutans* GS-5. The by-product calculus which forms between the teeth and gums is the major cause of gingivitis which is the inflammatory action which results in swelling, redness, cellular exudate and bacterial growth.

The only effective method known to control the mal effects of plaque in the mouth is mechanical removal. Daily brushing, flossing and irrigation using a toothbrush, toothpick, dental floss and water picks are effective in retarding the formation of caries and gum diseases. Such treatment if carried out improperly over long periods of time also causes damage to the gums by the abrasive action of brush bristles, floss and picks. Tooth erosion may be caused by the abrasives usually contained in conventional toothpaste.

In its broadest description the present invention is directed to a method of removing and reducing the formation of plaque and calculus in the oral cavity. The invention also provides for dentifrice compositions useful in reducing and removing plaque from the mouth surfaces and resultant irritation caused by plaque formation. It is further contemplated that the invention includes a method for treating the throat to relieve irritation.

Specifically, the invention involves a method for relieving throat irritations and inhibiting the formation of plaque and calculus which comprises regularly treating the surfaces of the teeth, mouth, gums and throat of mammals with a composition containing an effective amount of a monoalkyl or dialkyl isohexide having the general formula:

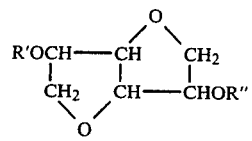

Formula I wherein R' and R" may be individually selected from the group consisting of —CH$_3$, —C$_2$H$_5$, —C$_3$H$_7$, —C$_4$H$_9$ and alternatively —H when the other R' or R" is an alkyl group of 1–4 carbon atoms. The invention also includes a dentifrice, gum, or confection which contains as an essential ingredient a compound of Formula I. The invention further includes a method for inhibiting the proliferation of bacteria especially *S-mutans* in the mouth by contacting the surfaces of the mouth with a prophylactic amount of a compound of Formula I.

The essential compounds used in the practice of the invention are monoalkyl and dialkyl ethers of 1,4,3,6-dianhydrohexitols of D-glucitol, D-mannitol, and L-iditol. These compounds are also referred to as mono and dialkyl ethers of isosorbide, isomannide and isoidide. For example, preparations of essentially pure dimethylisosorbide (DMI) may contain 1 to 2% by weight dimethyl isomannide, 1–2% by weight dimethyl isoidide, and 1–2% by weight of the monomethyl equivalents.

The compounds of the invention specifically include methylisosorbide, dimethylisosorbide, ethylisosorbide, diethylisosorbide (DEI), propylisosorbide, dipropylisosorbide, monoisopropylisosorbide, diisopropylisosorbide (DIPI), methylethylisosorbide, methylpropylisosorbide, ethylpropylisosorbide, butylisosorbide, dibutylisosorbide, isobutylisosorbide, diisobutylisosorbide, methylbutylisosorbide, ethylbutylisosorbide, propylbutylisosorbide, and the equivalent isomannide and isoidide modifications.

These compounds are conveniently made by the conventional Williamson ether synthesis technique and modifications thereof wherein a dianhydrohexitol is reacted with an alkyl halide or sulfate, or a mixture of alkyl halides or sulfates, in strong alkali followed by conventional purification and distillation techniques. Dimethylisosorbide is commercially available.

The tetraether compounds are usually obtainable as clear water white liquids having a pleasant odor and mouthfeel. Aqueous dilutions are as effective as pure liquids when applied to teeth. Dimethylisosorbide is considered non-toxic and is considered to be neither a primary irritant to human skin nor a skin sensitizer. In vivo testing with dimethylisosorbide at 100%, 80%, 50%, 25% and 10% aqueous solutions in toothdrops, toothpaste and mouthwash has produced no contraindications.

Dentifrice formulations containing the materials of Formula I may be in the form of a toothpaste, toothpaste gel, toothdrops, mouthwash, gargle, chewing gum, hard candy and soft candy. These formulations may contain from 5 to 95% by weight of the compounds of Formula I and at least two additional ingredients to improve taste, mouthfeel and effectiveness as a prophylactic. Such ingredients include water, solvents, stabilizers, coloring agents, flavoring agents, medicaments, astringents, detergents, polishing agents, sweeteners, gelling agents, thickeners, pigments and other antibacterial agents. Such combinations may be in the form of a thin liquid, paste, gel or taffy, supported on a solid particulate, (e.g., sugar or granular mannitol), wood (e.g., toothpicks), string (e.g., such as the type used in dental floss), or masticatory substances.

Mouthwashes and gargles are effective at concentrations of 5-90% by weight of the Formula I compounds in aqueous or alcoholic solution or other suitable liquid. Any usable liquid formulation containing the compound of Formula I for bathing, rinsing or gargling the tissues of the mouth or throat without injury is included within the scope of the invention. The formulations may include such other agents as propylene glycol, glycerine, ethylenediaminetetraacetic acid, methylparaben, detergents, coloring agents and flavors. Of course, the formulation may include other well known astringents and medicaments such as soluble salts including the ascorbates, citrates, tartrates, chlorides, fluorides, bromides, sulfates, and phosphates of metals selected from sodium, potassium, lithium, magnesium and calcium. Popular flavors include peppermint, wintergreen, orange, lime, cherry, strawberry, cinnamon, clove, anise and the like. Appropriate coloring agents may be added e.g., to match the flavor.

Typical formulations are illustrated but not limited to those of the following examples wherein all proportions are in parts by weight unless otherwise specified. Abbreviations used have their customary meanings.

In Examples 1-30 it should be understood that the proportions of ingredients shown at the left column is the same for column examples to the right in each Table unless otherwise specified.

TABLE I

| | Examples 1-5 | | | | | | | | | |
|---|---|---|---|---|---|---|---|---|---|---|
| | 1 | | 2 | | 3 | | 4 | | 5 | |
| Ingredients | Wt/g | Wt. % | Wt/g | Wt. % | Wt/g | Wt. % | Wt/g | Wt. % | Wt/g | Wt. % |
| Water (Distilled) | 1400 | | 1400 | | 1100 | | 600 | | 0 | |
| Sodium Benzoate USP | 4 | | | | | | | | | |
| Saccharin, Sodium USP | 50 | | | | | | | | | |
| Citric Acid (Anhydrous Grade) | 2 | | | | | | | | | |
| TWEEN ® 60 (Surfactant) | 8 | | | | | | | | | |
| Peppermint Oil (Fritzschi H-672) | 3.4 | | | | | | | | | |
| Clove Oil USP (Amend) | .6 | | | | | | | | | |
| Dimethylisorbide (Atlas G-100) | 200 | 10% | 100 | 5% | 500 | 25 | 1000 | 50 | 1800 | 90% |
| Ethyl Alcohol | 200 | | | | | | | | 0 | |
| Green Color (0.5 g FD & C Green in 500 gm H$_2$O) | 2 | | | | | | | | | |
| Water (distilled) q.s. to 2000 mls. | 130 | | 230 | | 130 | | 130 | | 130 | |

TABLE II

| | Examples 6-10 Mouthwash | | | | | | | | | |
|---|---|---|---|---|---|---|---|---|---|---|
| | 6 | | 7 | | 8 | | 9 | | 10 | |
| Ingredients | Wt/g | Wt. % | Wt/g | Wt. % | Wt/g | Wt. % | Wt/g | Wt. % | Wt/g | Wt. % |
| Water (Distilled) | 1400 | | 1400 | | 1100 | | 600 | | 0 | |
| Sodium Benzoate USP | 4 | | | | | | | | | |
| Saccharin, Sodium USP | 50 | | | | | | | | | |
| Citric Acid (Anhydrous Grade) | 2 | | | | | | | | | |
| TWEEN ® 60 (Surfactant) | 8 | | | | | | | | | |
| Peppermint Oil (Fritzschi H-672) | 3.4 | | | | | | | | | |
| Clove Oil USP (Amend) | .6 | | | | | | | | | |
| Diethyl Isosorbide | 200 | 10% | 100 | 5% | 500 | 25 | 1000 | 50 | 1800 | 90% |
| Ethyl Alcohol | 200 | | | | | | | | 0 | |
| Green Color (0.5 g FD & C Green in 500 gm H$_2$O) | 2 | | | | | | | | | |
| Water (distilled) q.s. to 2000 mls. | 130 | | 230 | | 130 | | 130 | | 130 | |

TABLE III

| | Examples 11-15 Mouthwash | | | | | | | | | |
|---|---|---|---|---|---|---|---|---|---|---|
| | 11 | | 12 | | 13 | | 14 | | 15 | |
| Ingredients | Wt/g | Wt. % | Wt/g | Wt. % | Wt/g | Wt. % | Wt/g | Wt. % | Wt/g | Wt. % |
| Water (Distilled) | 1400 | | 1400 | | 1100 | | 600 | | 0 | |
| Sodium Benzoate USP | 4 | | | | | | | | | |
| Saccharin, Sodium USP | 50 | | | | | | | | | |
| Citric Acid (Anhydrous Grade) | 2 | | | | | | | | | |
| TWEEN ® 60 (Surfactant) | 8 | | | | | | | | | |
| Peppermint Oil (Fritzschi | 3.4 | | | | | | | | | |

TABLE III-continued

Examples 11-15 Mouthwash

| Ingredients | 11 Wt/g | 11 Wt. % | 12 Wt/g | 12 Wt. % | 13 Wt/g | 13 Wt. % | 14 Wt/g | 14 Wt. % | 15 Wt/g | 15 Wt. % |
|---|---|---|---|---|---|---|---|---|---|---|
| H-672) | | | | | | | | | | |
| Clove Oil USP (Amend) | .6 | | | | | | | | | |
| Diisopropyl isosorbide | 200 | 10% | 100 | 5% | 500 | 25 | 1000 | 50 | 1800 | 90% |
| Ethyl Alcohol | 200 | | | | | | | | 0 | |
| Green Color (0.5 g FD & C Green in 500 gm H$_2$O) | 2 | | | | | | | | | |
| Water (distilled) q.s. to 2000 mls. | 130 | | 230 | | 130 | | 130 | | 130 | |

TABLE IV

Examples 16-20 Mouthwash

| Ingredients | 16 Wt/g | 16 Wt. % | 17 Wt/g | 17 Wt. % | 18 Wt/g | 18 Wt. % | 19 Wt/g | 19 Wt. % | 20 Wt/g | 20 Wt. % |
|---|---|---|---|---|---|---|---|---|---|---|
| Water (Distilled) | 1400 | | 1400 | | 1100 | | 600 | | 0 | |
| Sodium Benzoate USP | 4 | | | | | | | | | |
| Saccharin, Sodium USP | 50 | | | | | | | | | |
| Citric Acid (Anhydrous Grade) | 2 | | | | | | | | | |
| TWEEN ® 60 (Surfactant) | 8 | | | | | | | | | |
| Peppermint Oil (Fritzschi H-672) | 3.4 | | | | | | | | | |
| Clove Oil USP (Amend) | .6 | | | | | | | | | |
| Methyl-butyl isosorbide | 200 | 10% | 100 | 5% | 500 | 25 | 1000 | 50 | 1800 | 90% |
| Ethyl Alcohol | 200 | | | | | | | | 0 | |
| Green Color (0.5 g FD & C Green in 500 gm H$_2$O) | 2 | | | | | | | | | |
| Water (distilled) q.s. to 2000 mls. | 130 | | 230 | | 130 | | 130 | | 130 | |

TABLE V

Examples 21-25 Mouthwash

| Ingredients | 21 Wt/g | 21 Wt. % | 22 Wt/g | 22 Wt. % | 23 Wt/g | 23 Wt. % | 24 Wt/g | 24 Wt. % | 25 Wt/g | 25 Wt. % |
|---|---|---|---|---|---|---|---|---|---|---|
| Water (Distilled) | 1400 | | 1400 | | 1100 | | 600 | | 0 | |
| Sodium Benzoate USP | 4 | | | | | | | | | |
| Saccharin, Sodium USP | 50 | | | | | | | | | |
| Citric Acid (Anhydrous Grade) | 2 | | | | | | | | | |
| TWEEN ® 60 (Surfactant) | 8 | | | | | | | | | |
| Peppermint Oil (Fritzschi H-672) | 3.4 | | | | | | | | | |
| Clove Oil USP (Amend) | .6 | | | | | | | | | |
| Monopropyl Isosorbide | 200 | 10% | 100 | 5% | 500 | 25 | 1000 | 50 | 1800 | 90% |
| Ethyl Alcohol | 200 | | | | | | | | 0 | |
| Green Color (0.5 g FD & C Green in 500 gm H$_2$O) | 2 | | | | | | | | | |
| Water (distilled) q.s. to 2000 mls. | 130 | | 230 | | 130 | | 130 | | 130 | |

TABLE VI

Examples 26-30

| Ingredients | 26 Wt/g | 26 Wt. % | 27 Wt/g | 27 Wt. % | 28 Wt/g | 28 Wt. % | 29 Wt/g | 29 Wt. % | 30 Wt/g | 30 Wt. % |
|---|---|---|---|---|---|---|---|---|---|---|
| Water (Distilled) | 1400 | | 1400 | | 1100 | | 600 | | 0 | |
| Sodium Benzoate USP | 4 | | | | | | | | | |
| Saccharin, Sodium USP | 50 | | | | | | | | | |
| Citric Acid (Anhydrous Grade) | 2 | | | | | | | | | |
| TWEEN ® 60 (Surfactant) | 8 | | | | | | | | | |
| Peppermint Oil (Fritzschi H-672) | 3.4 | | | | | | | | | |
| Clove Oil USP (Amend) | .6 | | | | | | | | | |

TABLE VI-continued

| | Examples 26-30 | | | | | | | | | |
|---|---|---|---|---|---|---|---|---|---|---|
| | 26 | | 27 | | 28 | | 29 | | 30 | |
| Ingredients | Wt/g | Wt. % | Wt/g | Wt. % | Wt/g | Wt. % | Wt/g | Wt. % | Wt/g | Wt. % |
| Ethylmethyl isosorbide | 200 | 10% | 100 | 5% | 500 | 25 | 1000 | 50 | 1800 | 90% |
| Ethyl Alcohol | 200 | | | | | | | | 0 | |
| Green Color (0.5 g FD & C Green in 500 gm H$_2$O) | 2 | | | | | | | | | |
| Water (distilled) q.s. to 2000 mls. | 130 | | 230 | | 130 | | 130 | | 130 | |

The clear liquid mouthwash formula of Example 1 was used by five adult subject volunteers for a period of three months at least two times a week. Each reported a long lasting pleasing after-taste and mouthfeel. It was especially noticed that the tongue and teeth remained clean and free of deposit for several hours after each use. The products of Examples 2-30 are expected to provide equivalent performance.

Dental creams and gels are solutions of the compounds of Formula I which are thickened to a desired consistency. They range from clear liquids and free flowing gels having only thickener, color and flavor to a thick paste having pigment, abrasives, thickeners, medicaments, flavors, colors, vehicles, preservatives, humectants, surfactants, detergents, antioxidants, salts, sweetening agents, polishing agents and the like.

Thickening agents include hydroxyethyl cellulose, hydroxymethyl cellulose, synthetic gum, gum-like material such as Irish moss, gum tragocanth, xanthan, polyvinylpyrrolidone, starch polyvinylpolymers and finely divided silicas such as silica aerosols.

Pigments include alumina, hydrated alumina, zirconia, titania, colored lakes on alumina and titania, e.g., Red 2 G on alumina or FD and C Red 19 on titania.

Surface active agents include such organic anionic, cationic, nonionic and ampholytic compounds to provide detersive and foaming action to achieve increased prophylactic action. These may be selected from fatty acid monoglycerides, monosulfate salts, salts of dodecyl benzene sulfonate, aliphatic acylamides, ethanolamine salts of fatty acids, ethyloxide/propyloxide polyether derivatives of polyol esters, polyether derivatives of propylene diamine, and the like. The concentrations of these surfactants usually range from 0.05-5% by weight of the composition.

A variety of flavorings and/or sweeteners may be used in the paste or gel. Examples of flavoring oils include spearmint, peppermint, wintergreen, sassafras, clove, sage, anise, orange, eucalyptus, majoram, cinnamon, lemon, methylsalicylate and chloroform. Examples of sweeteners include sugar, lactose, maltose, maltitol, sorbitol, hydrogenated starch hydrolysates, sodium cyclamate, aspartame, perillartine, saccharine and corn syrup. These additions are used in concentrations of 0.01-5% by weight.

Medications and treating agents to protect teeth from decay are used in concentrations ranging from 0.01-1% by weight. Examples include fluorides of sodium, potassium, tin and sodium monofluorophosphate.

Typical antibacterial agents include $N^1$-(4-chlorobenzyl)-$N^5$-(2,4-dichlorobenzyl biguanide; p-chlorophenyl biguanide; 4-chlorobenzhydril biguanide; 4-chlorobenzhydrilguanilurea; N-3-lauryloxypropyl-$N^5$-p-chlorobenzyl biguanide; similar known antibacterial agents and their nontoxic acid addition salts.

EXAMPLES 31-45

Gelled Dentifrice

Gelled toothpaste was prepared in three lots (Examples 31-33) containing 5%, 10% and 25% by weight dimethylisosorbide (DMI) by mixing 60, 120 and 300 gram portions respectively of DMI with 20.4 gms peppermint oil, 3.6 gms clove oil, 3 gms sodium saccharine, 2.4 gms sodium benzoate, 42 gms sodium hydroxypropyl cellulose thickener and water to make 1200 gms. The gels were prepared by first mixing the selected amount of DMI, with the peppermint oil and clove oil portions. To this mixture were added the water, saccharine and sodium benzoate portions. The sodium hydroxypropyl cellulose thickeners were added with vigorous stirring to form a smooth gel. The gel was then permitted to stand for about 24 hours and thereafter packaged into 1 ounce collapsible aluminum tubes for use.

Gel compositions of Examples 31-33, and pure 100% DMI were applied to toothbrushes by twelve adult volunteers labelled Subject A-L in Table VII and applied as they would normally in brushing (Examples 34-45). In the case of the 100% liquid several drops were placed on the brush. The gelled compositions were easier to apply to the brush as expected. In each case moderate foaming occurred and is considered sufficient to provide adequate removal of plaque and food particles which accumulate. In some cases the 100% DMI was considered too strong while anything less than 5% DMI was too mild. The most satisfactory results were obtained by using 10-50% DMI in gels.

Each subject noticed an immediate improvement in mouth and teethfeel. Teeth were described as squeaky clean (the feeling obtained after professional cleaning) after 2-3 days brushing and remained that way for the duration of use. When test subjects resumed the use of commercially available toothpaste they noticed a return to a normal gritty film on the teeth after 4 days or sooner. Two subjects brushed once and did not continue the test. Five subjects were examined professionally after using the DMI containing tooth cleaner. Very little plaque was noticed. Even the back molars which are difficult to reach with a brush remained substantially free of plaque. In all cases gums appeared healthy.

A summary of testimonials given by the test subjects is outlined in Table VII wherein the first column indicates the age and sex of the subjects, the remaining columns indicate the months of use, the DMI concentration in the tooth cleaner and number of brushings per day (i.e., 100/2 means 100% DMI 2times/day) and the last column lists the comments.

TABLE VII

In Vivo Testing
Examples 34-45

| Example | Subject | M/F-Age | 1 % DMI/No. Wash/Day | 2 | 3 | 4 | 5 | 6 | 7 | 8 | Comments* |
|---|---|---|---|---|---|---|---|---|---|---|---|
| 34 | A | M/59 | 100/2 | 50/2 | 25/2 | 10/2 | 10/2 | 10/2 | 10/2 | 10/2 | A, B, E |
| 35 | B | F/55 | 100/2 | 100/2 | 10/2 | 10/2 | 10/2 | 10/2 | 10/2 | | A, B, E |
| 36 | C | M/56 | 100/2 | 100/2 | 100/2 | 10/2 | 10/2 | 10/2 | 10/2 | 10/2 | A, B, E |
| 37 | D | F/25 | 100/2 | 100/2 | 100/2 | 10/2 | 10/2 | 10/2 | 10/2 | 10/2 | A, B, E |
| 38 | E | M/30 | 100/2 | 100/2 | 100/2 | 10/2 | 10/2 | 10/2 | 10/2 | 10/2 | A, B, E |
| 39 | F | M/50 | 100/2 | 100/2 | 100/2 | 10/2 | 10/2 | 10/2 | 10/2 | 10/2 | A, B, E |
| 40 | G | F/49 | 10/2 | 10/2 | 10/2 | 10/2 | | | | | A, B, E |
| 41 | H | M/50 | 10/2 | 10/2 | 10/2 | 10/2 | | | | | A, B, E |
| 42 | I | M/47 | 25/2 | 25/2 | 25/2 | 25/2 | | | | | C, D |
| 43 | J | M/51 | 10/2 | 10/2 | | | | | | | A, B, E |
| 44 | K | M/45 | 10/2 | 10/2 | 10/2 | | | | | | A, B, E |
| 45 | L | M/45 | 10/2 | | | | | | | | A, B, E |

*Comments
A - Reduce plaque,
B - Gums healthy,
C - Gum bleeding stopped,
D - Typical heavy plaque former: Problem reduced to normal to light formation,
E - Tongue feels clean

EXAMPLE 46-48

| | Tooth Cleaning Drops | | |
|---|---|---|---|
| | 46 | 47 | 48 |
| Ingredient | (% by Wt.) | | |
| Dimethylisosorbide | 10 | 25 | 50 |
| Peppermint Oil NF | 1.5 | 1.5 | 1.5 |
| Clove Oil NF | 0.3 | 0.3 | 0.3 |
| Sodium Saccharine NF | 0.2 | 0.2 | 0.2 |
| Sodium Benzoate NF | 0.2 | 0.2 | 0.2 |
| Water (distilled) q.s. to 100 | | | |

Tooth cleaning drops were made by first dissolving the flavor oils in dimethylisosorbide, second dissolving the sodium salts in half the required water, third mixing the two portions and then adding water to full weight of 100 gms.

Additional formulations containing 5 and 90% DMI were considered too weak or too strong by some test subjects, however, even they appeared to be effective. Other formulation Examples 49-56 are presented with other active compounds of Formula I. Each active is combined with the additive as shown at the top of the left column in preparation indicated.

Examples 49-56
Tooth Cleaning Solution

| Ingredients | Example No. | 49 | 50 | 51 | 52 | 53 | 54 | 55 | 56 |
|---|---|---|---|---|---|---|---|---|---|
| Peppermint Oil NF | 1.5 | | | | | | | | |
| Clove Oil NF | .3 | | | | | | | | |
| Sodium Saccharin NF | 0.2 | | | | | | | | |
| Sodium Benzoate NF | 0.2 | | | | | | | | |
| Water (Distilled) q.s. to 100 | | | | | | | | | |
| Active | | | | | | | | | |
| Diethylisosorbide | | 10 | | | | | | | |
| Diisopropylisosorbide | | | 5 | | | | | | |
| Methylethylisosorbide | | | | 25 | | | | | |
| Monomethylisosorbide | | | | | 75 | | | | |
| Monobutylisosorbide | | | | | | 85 | | | |
| Dibutylisosorbide | | | | | | | 15 | | |
| Dimethylisosorbide | | | | | | | | 90 | |
| Monomethylisosorbide | | | | | | | | | 95 |

EXAMPLES 57-59

| | Conventional Toothpaste | | |
|---|---|---|---|
| | 57 | 58 | 59 |
| Ingredients | Parts by Wt. | | |
| Dimethylisosorbide (DMI) | 10 | 25 | 50 |
| Cellulose gum, CMC - 7MF | 1.25 | 1.25 | 1.25 |
| Glycerine | 5.0 | 5.0 | 5.0 |
| Magnesium Aluminum silicate | 0.25 | 0.25 | 0.25 |
| 70% Sorbitol Solution USP | 30.0 | 30.0 | 30.0 |
| Dicalcium phosphate dihydrate | 28.0 | 28.0 | 28.0 |
| Dicalcium phosphate (Anhydrous) | 20.0 | 20.0 | 20.0 |
| Sodium Lauryl Sulfate | 1.0 | 1.0 | 1.0 |
| Sodium Saccharine | 0.2 | 0.2 | 0.2 |
| Flavor | q.s. | q.s. | q.s. |
| Water | q.s. | q.s. | q.s. |

To make a conventional toothpaste the above quantity of cellulose gum is dispersed in glycerine. The magnesium aluminum sulfate is dispersed in water under high shear. These two components are mixed with the DMI and sorbitol solution and thereafter with the remaining ingredients listed above. Water is then added in a conventional mixer to obtain the desired paste viscosity. Fluoride salts may be added to the formulation for prevention of caries. Concentrations as low as 5% of DMI in such paste formulations are effective. Similar concentrations of Formula I compounds such as diethyl-, diisopropyl-, dibutyl-, methylbutyl-, or monobutyl isosorbide may be employed with equivalent effectiveness and may be incorporated into many equivalent opaque and clear gel formulations.

EXAMPLE 60

| | Clear Gel Toothpaste |
|---|---|
| Ingredients | % by Wt. |
| Dimethylisosorbide | 10 |
| Cellulose gum CMC-9M31XF | 0.3 |
| Glycerine | 3 |
| 70% Sorbitol/water solution USP | 30 |
| Water | .3 |
| Sodium benzoate | .2 |
| Sodium saccharine | .2 |
| 70% Sorbitol/water solution USP | 30 |
| Polyethylene glycol 1540 | 5.0 |

-continued

| Clear Gel Toothpaste | |
|---|---|
| Ingredients | % by Wt. |
| Hydrated silica (Syloid ® B-30) | 14.0 |
| Hydrated silica (Syloid ® 244) | 8.5 |
| Flavor | q.s. |
| 70% Sorbitol/water solution USP | 6.0 |
| Sodium lauryl sulfate | 1.5 |

Clear gel formulations may be made by adding the above-listed ingredients together as follows:

Disperse cellulose gum in glycerin, blend 30.2 g. sorbitol, water, dimethylisosorbide, sodium benzoate, sodium saccharine and mix into a uniform dispersion to form a first portion. Mix 30 g. of sorbitol with the polyethylene glycol 1540 using moderate heat and agitation. Add this mixture to the first portion and stir until uniform consistency.

Dry blend the silicas. Using a Hobart type mixer or equivalent and add the previously mixed materials. When a smooth gel develops add flavors, additional sorbitol and sodium lauryl sulfate.

Blend the mixture with minimum agitation until uniform consistency. Condition the resulting gel overnight at 50° C. Heat to 65° C. and deaerate under vacuum. A Versator (Cornell Machine Company) or equivalent apparatus effectively deaerates this gel system.

EXAMPLES 61-64

| Nonabrasive Toothpaste Gel | | | | |
|---|---|---|---|---|
| Ingredients (% by wt.) | 61 | 62 | 63 | 64 |
| Peppermint Oil NF | 1.5 | | | |
| Clove Oil NF | .3 | | | |
| Sodium saccharin NF | .2 | | | |
| Sodium benzoate NF | .2 | | | |
| Klucel MF Thickener (cellulose polymer) | 2.5 | | | |
| Sodium lauryl sulfate | 1.5 | | | |
| Water q.s. 100 | | | | |
| Dimethylisosorbide | 10 | | | |
| Diethylisosorbide | | 10 | | |
| Diisopropylisosorbide | | | 10 | |
| Dibutylisosorbide | | | | 10 |

Nonabrasive gels are prepared by blending active isosorbide actives in amounts shown above with peppermint and clove oils. This blend is added to a mixture of water, sodium lauryl sulfate, saccharin and sodium benzoate. To this is added cellulose polymer thickener until a smooth gel forms. Add additional water to adjust active concentration, allow bulk to sit for 24 hours and place in suitable containters. Fluorides may be added to this system. The gels appear to be very effective without added detergent. Gel viscosity can be adjusted by reducing or increasing thickened concentration.

Throat and mouth treatments with the compounds of Formula I may be carried out in blends with soft candy substances in the form of nonconsumable material such as chewing gum and bubble gum or as a consumable confection such as taffy, caramels, gumdrops, etc. These items provide an excellent way of treating the teeth and gums especially where plaque and calculus formation is greatest.

A chewing gum formula normally comprises a gum base, sweetener, plasticizer and Formula I compound. Chewing gum base is a blend of synthetic and natural products coming within the Food, Drug and Cosmetic Law 21 CFR 121.1054. It contains masticatory substances such as natural (coagulated or concentrated) lattices of vegetable origin, e.g., Chicle, Perillo and natural rubber to name a few. Synthetic lattices such as butadiene-styrene rubber, butyl rubber, paraffin, polyvinylacetate, polyvinylethylene, blends of these and others may also be used. Further materials which may be included are plasticizing materials such as glycerol esters of rosin, terpine resins and antioxidants such as butylated hydroxy anisol. The chewing gums may also contain coloring agents, pigments, flavor and sweeteners both artificial and natural as named above.

EXAMPLE 65

| Chewing Gum | |
|---|---|
| Ingredients | % By Wt. |
| Gum base | 25 |
| 70% Sorbitol/water solution | 11 |
| Dimethylisosorbide | 10 |
| Crystalline Sorbitol NF | 53 |
| Glycerine NF | 0.5 |
| Flavor | q.s. |

The gum base was mixed in a small mixer and heated in a water bath at 38° C. After mixing for four minutes, flavoring was added and mixing was continued for 2 minutes. The mixture was heated to 43° and cast into sticks on a flat plate.

Suitable gums may also be prepared using sugar in place of the sorbitol solution. It is recognized, however, that a chewing gum free of sugar provides a poorer environment for the formation of dental plaque.

Edible gums comprise any of a number of colloidal polysaccharide substances of plant origin that are gelatinous when moist but hard when dry, for example, gum arabic.

Taffy, nougats and caramels are derived from boiled sugars such as molasses and brown sugar which are pulled to incorporate air and cast into blocks; these may also incorporate conventional fruit flavors, or chocolate or vanilla. The dianhydrohexitol ethers of Formula I may be incorporated with masticatory substances at any convenient point of manufacture in concentrations ranging from 5-25% by weight in regular formulations.

EXAMPLE 66

| Nougat | |
|---|---|
| Ingredients | (Parts by Wt.) |
| I | |
| Corn syrup | 5 |
| Honey | 10 |
| Dried egg albumen | 1 |
| Water | 4 |
| II | |
| Sugar | 40 |
| Corn syrup | 30 |
| Water | 10 |
| III | |
| Vanilla flavoring | .18 |
| Hard vegetable butter 92° C. | 3.0 |
| Nuts | 12.0 |
| Dimethylisosorbide | 11.5-22.5 |

Part I is made by dissolving egg albumen in the specified amount of water and cooking the honey and corn syrup to 116° C. Place in bowl of mixer and heat to at least 71° C. Slowly add dissolved egg albumen. Beat until batch is light and fluffy.

To manufacture Part II, cook sugar and syrup to 130° C. Add the sugar and syrup mixture slowly to the beaten egg white mixture. Continue beating until batch begins to stiffen.

To manufacture Part III, add together in the order named dimethyl isosorbide, flavoring, melted hard butter and nuts. After mixing butter and nuts into batch, pour into trays that have been dusted with starch and lined with edible wafer paper. Pour at least three centimeters deep. Cover the top of the batch with wafer paper. Let set for two days to ripen. Take solidified material out of the trays and cut into blocks about 2 centimeters square. Wrap in wax paper or moisture proof cellulose wrappers.

About 2.5–10% based on the total formula weight of the Formula I ingredients could be added for taffy and marshmallow.

EXAMPLE 67

| Chewable Tablet | |
|---|---|
| Ingredients | Per Tablet (mg.) |
| Dimethylisosorbide | 20 |
| Wintergreen oil | 0.6 |
| Menthol | 0.85 |
| Peppermint oil | 0.3 |
| Silica (Syloid 244) | 1.0 |
| Sodium saccharin | 0.3 |
| Sodium bicarbonate | 14.0 |
| Mannitol, USP (Granular) | 160.95 |
| Calcium stearate | 2.0 |

Mix dimethylisosorbide, flavoring oils and menthol to form a clear liquid. Absorb the mixture on silica and add the remaining ingredients. Blend and compress the mixture on 1 centimeter flat beveled edge punch to a thickness of about 3.1 millimeters.

EXAMPLE 68

| Sugarless Hard Candy | |
|---|---|
| Ingredients | % By Wt. |
| 70% Sorbitol in aqueous solution | 86–99 |
| Dimethylisosorbide | 10 |
| citric acid | 0.5–1.5 |
| Crystalline Sorbitol Seed grade | .5 |
| Flavoring | .2–1 |
| Color | q.s. |

Weigh out the appropriate amount of sorbitol solution and transfer it to a cooking vessel. Avoid scorching the batch causing yellowing of the solution. Begin cooking it using low heat until the sorbitol solution has been warmed to 70° C. Then apply sufficient heat to heat the solution to 163° C., at which point the moisture is approximately 3.0%.

Cool the cooked batch evenly and with agitation using tempered water at about 65°–70° C. which is circulating in a jacket placed around the cooking vessel. If anhydrous citric acid is used add it to the batch while cooling when the temperature is about 140°–146° C. Hold the batch at this temperature until all the crystals have melted. Continue to cool the batch to 87° C. It is important that (a) the batch not be supercooled by using cold water to lower the batch temperature with good agitation; and (b) agitation be kept to a minimum to avoid entrapment of large quantities of air which will ruin clarity.

After the batch is cooled to 88° C., add 0.5% crystalline sorbitol seed grade slowly to the batch while mixing thoroughly with slow agitation. The seed will nucleate the melt. Once the seed is added, check the melt temperature and adjust the temperature to 88° plus or minus 1° C., being careful not to overheat the melt above 92° C., destroying the seed crystal. Coloring and flavoring are then added to the melt. Any other optional ingredients may be added at this point or if they are heat stable added to the melt while it is being cooled to between 135° and 115° C. During this cool down period the dimethylisosorbide is blended in. The melt should then be deposited into molds which have been brought to room temperature to avoid super cooling. Melts deposited into molds which have been chilled even 2°–3° C. below room temperature will take longer to set up. Once deposited, if the mold is maintained in an area with a temperature of 24°–27° C. and a relative humidity of 40–45%, the candy should be ready to demold in 20–30 minutes depending on the size, shape and type of mold used.

By allowing the hard candy to dissolve slowly in the mouth, a tingling mouthfeel takes place indicative of mouthwash and toothpaste as previously described. Frequent use of the candy will act to inhibit plaque formation in the same way as does the toothpaste and mouthwash.

As a further extension of this invention, it is possible and desirable to blend healing agents with the tetraether derivatives of Formula I in mouthwashes and toothpaste to stimulate healthy normal tissue formation. A demulcent healing agent found to be compatible with the tetraether derivatives of Formula I is Allantoin (glyoxyl-diureide) 5-ureidohydantoin a well known material sometimes prepared by the oxidation of uric acid. It is expected that when used in therapeutic concentrations of 0.1–2% by weight in dentifrices Allantoin will act to promote the healing of gum tissue.

EXAMPLES 69–71

| Allantoin Tooth Cleaning Drops | | | |
|---|---|---|---|
| | % By Weight | | |
| Ingredients | #69 | #70 | #71 |
| Allantoin | 0.2 | 0.5 | 0.1 |
| Dimethylisosorbide | 10.0 | 25.0 | 10.0 |
| Peppermint Oil NF | 1.5 | 1.5 | 1.5 |
| Clove Oil NF | 0.3 | 0.3 | 0.3 |
| Sodium Saccharine NF | 0.2 | 0.2 | 0.2 |
| Sodium Benzoate NF | 0.2 | 0.2 | 0.2 |
| Water (distilled) q.s. | | | |

Tooth cleaning drops are prepared by first dissolving Allantoin and the flavoring agents in dimethylisosorbide, second dissolving the sodium salts in half the required water, third mixing the two solutions together and fourth adding water to full volume by weight. The same procedure is followed for all formulations.

EXAMPLES 72–73

| Allantoin Toothpaste Gel | | |
|---|---|---|
| | % By Weight | |
| Ingredients | #72 | #73 |
| Dimethylisosorbide | 10 | 25 |
| Allantoin | .02 | 0.5 |
| Peppermint Oil NF | 1.5 | 1.5 |
| Clove Oil NF | 0.3 | 0.3 |

-continued

Allantoin Toothpaste Gel

| Ingredients | % By Weight | |
|---|---|---|
| | #72 | #73 |
| Sodium Saccharine NF | 0.2 | 0.2 |
| Sodium Benzoate NF | 0.2 | 0.2 |
| Klucel ® MF Thickener (Cellulose polymer) | 2.5 | 2.5 |
| Sodium Lauryl Sulfate | 1.5 | 1.5 |
| Water (distilled) q.s. | | |

Mix Allantoin, dimethylisosorbide, peppermint oil and clove oil. Dissolve sodium lauryl sulfate, saccharine, and sodium benzoate in water. Mix the two solutions well and add Klucel ® MF. Continue mixing until a smooth gel forms. Dilute the mixture to full volume with water and allow the bulk material to sit 24 hours. Fill suitable containers for storage.

Another embodiment of the invention pertains to coating dental floss with the tetraethers derivatives of Formula I. The dental profession has recognized the value of daily flossing between the teeth to clean out dental plaque and food debris. Coating dental floss with a therapeutic amount of a compound of Formuls I such as dimethylisosorbide will provide a method for making intimate contact between the teeth to capitalize on the solvent properties of the ether to wash away any bound foreign materials especially dental plaque.

EXAMPLES 74-76

Dental Floss

| Ingredients | % By Weight | | |
|---|---|---|---|
| | #74 | #75 | #76 |
| Dimethylisosorbide | 25 | 50 | 75 |
| Sodium Lauryl Sulfate NF | 1.5 | 1.5 | 1.5 |
| Peppermint Oil NF | 1.5 | 1.5 | 1.5 |
| Clove Oil NF | 0.3 | 0.3 | 0.3 |
| Sodium Saccharine NF | 0.2 | 0.2 | 0.2 |
| Sodium Benzoate NF | 0.2 | 0.2 | 0.2 |
| Water (distilled) q.s. | | | |

First mix the dimethylisosorbide and flavorings. Then dissolve the sodium lauryl sulfate, saccharine and benzoate in water. Mix the two solutions.

Pass the dental floss fiber through this solution into a suitable spool and package in a water tight closure. The floss should be used in the usual manner.

It has been shown that antigenic protein present on the cell walls and in cultures of Streptococcus mutans especially genetic group I (cyro types, c, e, and f) when separated from other antigenic proteins give an antigenic portion which may be used as a vaccine or to raise antibodies for use in protecting against dental caries in monkeys as demonstrated in U.S. Pat. No. 4,448,768. These antigenic materials are protein compounds remaining on the cell walls of Streptococcus mutans after extraction of the cell with sodium dodecyl sulfate in water for one hour at room temperature. They have a molecular weight of about 29,000±3,000. These may be administered to man or other mammals in doses of 1–50 micrograms per kilogram body weight to reduce the formation of dental caries in the immunized subject.

The dianhydrohexitol ethers used in the invention are effective in controlling plaque formation on the teeth by a method not clearly understood. However, accepting the fact that S. mutans as demonstrated above are responsible for the formation of caries in a sugar environment, a demonstration that the compositions of Formula I inhibit the activities of S. mutans would provide presumptive evidence for the above described theory.

A study was designed to determine the effectiveness of selected aliphatic ethers of Formula I as antimicrobial agents.

In one series of experiments the plaque producing microbe, Streptococcus mutans ATCC 27351 was grown in Brain-Heart Infusion Broth overnight (18 hours), at 37° C. Seven ten-milliliter aliquots were removed from the well agitated culture and used as an inoculum for each of the test reaction vessels. (Control, DMI, DEI, DIPI each at, 10 and 15%). The reaction vessels were water jacketed glass spinner flasks and were maintained at 37° C. by a circulating water bath. In this instance the chemicals to be tested were added within minutes of the inoculum. Microbial population data is tabulated in Table VIII.

In a second phase of this study Streptococus mutans was given an 18 hour "head start", i.e, the potential antimicrobial agents were added 18 hours after the inoculation of the reaction vessels. In each of the phases the microbial population (colony count) was monitored at 1, 3.5, 7.0, 22, 26, 46, 50, 70, 74, 94, and 98 hours. In phase two of the study DMI, DEI, DIPI, were tested at concentrations of 0 (Control), 1, 5, 10 and 15%.

TABLE VIII

REACTION VESSEL INOCULATED WITH STREPTOCOCCUS MUTANS FOLLOWED IMMEDIATELY BY CANDIDATE ANTIMICROBIAL
MICROBIAL POLUATION AFTER INOCULATION

| | | 0 | 3.5 | 7.0 | 22 | 26 | 46 | 50 | 70 | 74 | 94 | 98 | 118 Hrs. |
|---|---|---|---|---|---|---|---|---|---|---|---|---|---|
| Control | — | $1 \times 10^1$ | $<10$ | $1 \times 10^1$ | $1.7 \times 10^5$ | $8.5 \times 10^6$ | $1.0 \times 10^7$ | $2.0 \times 10^7$ | $7.5 \times 10^5$ | $2.0 \times 10^6$ | $1.0 \times 10^5$ | $7.0 \times 10^5$ | $5 \times 10^5$ |
| Dimethylisosorbide | 10% | $<10$ | $<10$ | $<10$ | $<10$ | $<10$ | $<10$ | $<10$ | $<10$ | $<10$ | $<10$ | $<10$ | $<10$ |
| Dimethylisosorbide | 15% | $<10$ | $<10$ | $<10$ | $<10$ | $<10$ | $<10$ | $<10$ | $<10$ | $<10$ | $<10$ | $<10$ | $<10$ |
| Diethylisosorbide | 10% | $<10$ | $<10$ | $<10$ | $<10$ | $<10$ | $<10$ | $<10$ | $<10$ | $<10$ | $<10$ | $<10$ | $<10$ |
| Diethylisosorbide | 15% | $<10$ | $<10$ | $<10$ | $<10$ | $<10$ | $<10$ | $<10$ | $<10$ | $<10$ | $<10$ | $<10$ | $<10$ |
| Diisopropylisosorbide | 10% | $<10$ | $<10$ | $<10$ | $<10$ | $<10$ | $<10$ | $<10$ | $<10$ | $<10$ | $<10$ | $<10$ | $<10$ |
| Diisopropylisosorbide | 15% | $<10$ | $<10$ | $<10$ | $<10$ | $<10$ | $<10$ | $<10$ | $<10$ | $<10$ | $<10$ | $<10$ | $<10$ |

TABLE IX

ANTIMICROBIAL* PROPERTIES OF VARIOUS ETHERS OF ISOSORBIDE

| | | 0 | 1.0 | 3.5 | 7.0 | 22 | 26 |
|---|---|---|---|---|---|---|---|
| Control | | $3.2 \times 10^8$ | $3.3 \times 10^8$ | $3.3 \times 10^8$ | $2.3 \times 10^8$ | — | |
| Dimethylisosorbide | 1% | — | $1.8 \times 10^8$ | $2.0 \times 10^8$ | $3.0 \times 10^8$ | $9.3 \times 10^7$ | — |
| | 5% | — | $1.4 \times 10^8$ | $1.3 \times 10^8$ | $1.5 \times 10^8$ | $1.0 \times 10^8$ | — |

TABLE IX-continued
ANTIMICROBIAL* PROPERTIES OF VARIOUS ETHERS OF ISOSORBIDE

| | | | | | | | |
|---|---|---|---|---|---|---|---|
| Diethylisosorbide | 10% | $9.2 \times 10^7$ | — | $9.2 \times 10^7$ | $9.0 \times 10^7$ | $3.1 \times 10^6$ | $6.3 \times 10^6$ |
| | 15% | $1.1 \times 10^8$ | — | $7.6 \times 10^7$ | $2.7 \times 10^7$ | $1.1 \times 10^4$ | $1.4 \times 10^3$ |
| | 1% | — | $1.6 \times 10^8$ | $2.0 \times 10^8$ | $3.1 \times 10^8$ | $9.7 \times 10^7$ | — |
| | 5% | — | $1.3 \times 10^8$ | $9.9 \times 10^7$ | $9.2 \times 10^7$ | $6.6 \times 10^7$ | — |
| | 10% | — | — | — | — | — | — |
| | 15% | $2.4 \times 10^8$ | — | $8.6 \times 10^7$ | $<10$ | $<10$ | |
| Diisopropylisosorbide | 1% | — | $1.3 \times 10^8$ | $1.3 \times 10^8$ | $1.1 \times 10^8$ | $9.6 \times 10^7$ | — |
| | 5% | — | $1.3 \times 10^8$ | $9.9 \times 10^7$ | $9.2 \times 10^7$ | $6.6 \times 10^7$ | — |
| | 10% | — | — | — | — | — | — |
| | 15% | $1.1 \times 10^8$ | — | $9.2 \times 10$ | $<10$ | $<10$ | $<10$ |

| | | 46 | 50 | 70 | 74 | 94 | 98 Hrs. |
|---|---|---|---|---|---|---|---|
| Control | | $1.3 \times 10^8$ | $1.8 \times 10^8$ | $1.5 \times 10^8$ | $1.4 \times 10^8$ | $6.1 \times 10^7$ | $5.7 \times 10^7$ |
| Dimethylisosorbide | 1% | $1.6 \times 10^8$ | $3.0 \times 10^7$ | $9.9 \times 10^7$ | $1.2 \times 10^8$ | $3.7 \times 10^8$ | $3.0 \times 10^8$ |
| | 5% | $1.2 \times 10^8$ | $1.3 \times 10^8$ | $1.4 \times 10^8$ | $1.2 \times 10^8$ | $8.5 \times 10^7$ | $8.6 \times 10^7$ |
| | 10% | $8.2 \times 10^4$ | $8.1 \times 10^4$ | $2.0 \times 10^3$ | $1.1 \times 10^3$ | $<10$ | $<10$ |
| | 15% | $<10$ | $<10$ | $<10$ | $<10$ | $<10$ | $<10$ |
| Diethylisosorbide | 1% | $1.2 \times 10^8$ | $2.1 \times 10^8$ | $1.8 \times 10^8$ | $1.6 \times 10^8$ | $1.0 \times 10^8$ | $9.7 \times 10^7$ |
| | 5% | $5.7 \times 10^7$ | $5.8 \times 10^8$ | $2.4 \times 10^8$ | $1.9 \times 10^8$ | $1.3 \times 10^8$ | $1.2 \times 10^8$ |
| | 10% | — | — | — | — | — | — |
| | 15% | $<10$ | $<10$ | $<10$ | $<10$ | $<10$ | $<10$ |
| Diisopropylisosorbide | 1% | $2.9 \times 10^8$ | $4.8 \times 10^8$ | $4.3 \times 10^8$ | $2.9 \times 10^8$ | $2.5 \times 10^8$ | $2.4 \times 10^7$ |
| | 5% | $5.7 \times 10^7$ | $5.8 \times 10^7$ | $2.4 \times 10^8$ | $1.9 \times 10^8$ | $1.3 \times 10^8$ | $1.2 \times 10^8$ |
| | 10% | — | — | — | — | — | — |
| | 15% | $<10$ | $<10$ | $<10$ | $<10$ | $<10$ | $<10$ |

*Approximately 18 hours was allowed between inoculation and antimicrobial addition.

Both experiments give an indication that the population of S. mutans is drastically reduced in the environment of the dianhydrohexitol derivatives employed in the treatment method and compositions of the invention.

Dissolution studies were carried out with dimethylisosorbide on harvested human dental calculus (tartar) that was collected and held in normal saline solution until ready for testing. The calculus was added to 100% dimethylisosorbide as well as a 50/50 solution of dimethylisosorbide/water and allowed to sit in a resting position with occasional stirring. The calculus slowly dissolved into the dimethylisosorbide over a 24-hour period (200 mg. in 100 ml. of solvent). This occurred in both solutions.

In another dissolution study extracted soiled human teeth were immersed in 100% dimethylisosorbide as well as a 50/50 solution of dimethylisosorbide/water. These solutions were stirred occasionally and observed for changes in appearance over a several week period. It was noted in particular that the part of the tooth that is exposed above the gum line, self-cleaned and became very clean and white after 24 to 36 hours. The bottom of the beaker became loaded with debris. It was also observed that dimethylisosorbide did not dissolve or loosen the fillings in the teeth. Each dilution appeared to be equally effective.

What is claimed is:

1. In a mouthwash or gargle formulation for inhibiting the formation of plaque and calculus and relieving throat irritation in the oral cavity of mammals which comprises at least two ingredients selected from the group consisting of water, stabilizers, coloring agents, flavoring agents, surfactants, astringents, detergents, medicaments, sweeteners and antibacterial agents, the improvement which consists essentially of including therewith and S. mutans inhibiting amount of a dianhydrohexitol compound having the general formula:

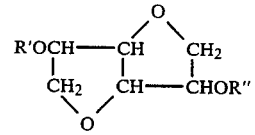

wherein R' and R" are individually selected from alkyl radicals selected from the group consisting of —CH$_3$, —C$_2$H$_5$, —C$_3$H$_7$, —C$_4$H$_9$ or —H when the other R' or R" is an alkyl radical of 1–4 carbon atoms.

2. A composition of claim 1 containing from 5–90% by weight of said dianhydrohexitol.

3. A composition of claim 1 wherein said dianhydrohexitol is selected from the group consisting of methyl isosorbide, dimethylisosorbide, ethylisosorbide, diethylisosorbide, isopropylisosorbide, diisopropylisosorbide, butylisosorbide, dibutylisosorbide, methylethylisosorbide, methylpropylisosorbide, methylbutylisosorbide, ethylpropylisosorbide and ethylbutylisosorbide.

4. A composition of claim 1 wherein said dianhydrohexitol is dimethylisosorbide.

5. A composition of claim 1 which includes ingredients selected from the group consisting of propylene glycol, glycerine, ethylenediaminetetracidic acid, and methylparaben.

6. A composition of claim 1 which includes astringents selected from water soluble salts selected from the group consisting of ascorbates, citrates, tartrates, chlorides, fluorides, bromides, sulfates and phosphates of metals selected from the group consisting of sodium, potassium, lithium, magnesium and calcium.

7. A composition of claim 1 including flavoring agents selected from the group consisting of peppermint, wintergreen, orange, lime, cherry, strawberry, cinnamon, clove, and anise.

8. A composition of claim 1 comprising distilled water, sodium benzoate, saccharin, citric acid, a surfactant, peppermint oil, clove oil, ethyl alcohol, and a coloring agent.

9. A composition of claim 1 which contains a therapeutic amount of allantoin.

* * * * *